(12) United States Patent
Schoen et al.

(10) Patent No.: US 12,111,292 B2
(45) Date of Patent: Oct. 8, 2024

(54) METHOD FOR DETERMINATION OF PROPERTIES OF CUTTINGS FROM ROCK DRILLING

(71) Applicant: THINK AND VISION GMBH, Leoben (AT)

(72) Inventors: Juergen Schoen, Leoben (AT); Christian Koller, Lannach (AT); Luis Arnaldo Gonzalez, Cracow (PL)

(73) Assignee: THINK AND VISION GMBH, Leoben (AT)

(*) Notice: Subject to any disclaimer, the term of this patent is extended or adjusted under 35 U.S.C. 154(b) by 288 days.

(21) Appl. No.: 17/769,286

(22) PCT Filed: Sep. 16, 2020

(86) PCT No.: PCT/EP2020/075846
§ 371 (c)(1),
(2) Date: Apr. 14, 2022

(87) PCT Pub. No.: WO2021/053005
PCT Pub. Date: Mar. 25, 2021

(65) Prior Publication Data
US 2022/0412854 A1    Dec. 29, 2022

(30) Foreign Application Priority Data

Sep. 17, 2019 (EP) .................... 19197841

(51) Int. Cl.
*G01N 3/06*    (2006.01)
*E21B 49/02*   (2006.01)
*G01N 33/24*   (2006.01)

(52) U.S. Cl.
CPC ............... *G01N 3/06* (2013.01); *E21B 49/02* (2013.01); *G01N 33/24* (2013.01); *G01N 2203/0087* (2013.01)

(58) Field of Classification Search
CPC .. G01N 3/06; G01N 33/24; G01N 2203/0087; E21B 49/02; E21B 49/003
(Continued)

(56) References Cited

U.S. PATENT DOCUMENTS 2,740,292 A  *  4/1956  Sewell ................. E21B 49/005
                                                      73/152.16
2009/0084168 A1*  4/2009  Bulled ..................... G01N 3/40
                                                          73/78

(Continued)

FOREIGN PATENT DOCUMENTS

DE    202015101542 U1  *  8/2016
EP    2 653 224           10/2013
(Continued)

OTHER PUBLICATIONS

International Search Report for PCT/EP2020/075846 mailed Dec. 22, 2020, 3 pages.
(Continued)

*Primary Examiner* — Marrit Eyassu
(74) *Attorney, Agent, or Firm* — NIXON & VANDERHYE

(57) ABSTRACT

In a method for determination of properties of cuttings from rock drilling the cuttings are crushed between at least two rollers, at least one roller being driven by a motor. A mechanic specific energy of the cuttings is determined by measuring the energy applied by the motor.

17 Claims, 3 Drawing Sheets

(58) Field of Classification Search
USPC .......................................................... 73/788
See application file for complete search history.

(56) References Cited

U.S. PATENT DOCUMENTS

| | | | | |
|---|---|---|---|---|
| 2010/0252325 A1* | 10/2010 | Porche | ................... | E21B 49/003 |
| | | | | 175/40 |
| 2015/0013448 A1* | 1/2015 | Smith | ................... | E21B 49/005 |
| | | | | 73/152.46 |
| 2019/0169986 A1* | 6/2019 | Storm, Jr. | .............. | G01V 11/00 |

FOREIGN PATENT DOCUMENTS

| | | | | | |
|---|---|---|---|---|---|
| EP | 2653224 A1 | * | 10/2013 | .............. | B02C 4/02 |
| WO | 2016/051345 | | 4/2016 | | |
| WO | 2017/035613 | | 3/2017 | | |
| WO | WO-2017035613 A1 | * | 3/2017 | .............. | B02C 4/02 |
| WO | 2017/102736 | | 6/2017 | | |

OTHER PUBLICATIONS

Written Opinion of the ISA PCT/EP2020/075846 mailed Dec. 22, 2020, 5 pages.
International Preliminary Report on Patentability for PCT/EP2020/075846 dated Mar. 15, 2022, 6 pages.
EP Search Report for EP19197841.0 dated Feb. 25, 2020, 6 pages.

* cited by examiner

METHOD FOR DETERMINATION OF PROPERTIES OF CUTTINGS FROM ROCK DRILLING

CROSS-REFERENCE RELATED TO PRIOR APPLICATIONS

This application is the U.S. national phase of International Application No. PCT/EP2020/075846 filed Sep. 16, 2020 which designated the U.S. and claims priority to EP 19197841.0 filed Sep. 17, 2019, the entire contents of each of which are hereby incorporated by reference.

BACKGROUND OF THE INVENTION

Field of the Invention

The invention relates to a method for determination of properties of cuttings from rock drilling in which the cuttings are crushed between two rollers driven by an electric motor.

Description of the Related Art

This invention relates in particular to drilling in mining, oil and gas industry and in particular to provide real-time drilling data in order to improve drilling operation. It is known from prior art to analyze the cuttings, ie material that has been removed at the lower end of a drill string, to obtain information of the rock being drilled which contributes significantly to a safe and optimized drilling process (WO 2017/102736 A1).

Mechanic specific energy (MSE) is an important rock parameter for a drilling process, in particular a measure of energy used to destroy an intact rock mass and one of the fundamental and general accepted parameters for characterization of penetrated rock mechanical properties.

The concept of specific energy was developed by Teale (1966) for drilling engineering, serving as a basis for further work in the area of drilling optimization. Several research papers (Dupriest and Koederitz, 2005; Pessier, 1992; Waughman et al., 2002) show the successful application of this concept to assess and optimize the drilling process using real field data, showing the advantages of this method. Emmanuel Detournay et al. (1996) used the concept of specific energy in the design and development of the rock strength device used to perform scratch tests on rocks.

In drilling engineering, MSE can be calculated as follows:

$$MSE = \frac{WOB}{A_B} + \frac{120 * \pi * RPM * T}{A_B * ROP}$$

where:
WOB=weight on bit,
$A_B$=bit cross-sectional area,
RPM=revolutions per minute of the drilling bit,
ROP=rate of penetration,
T=bit torque.

If MSE is calculated this way MSE relates to the energy actually applied to the drilling progress. Commonly it is determined from surface drilling data and therefore includes all energy consuming components of the process which influence the measurements/calculations of energy (e.g. vibration).

SUMMARY OF THE INVENTION

It is therefore an object of the invention to provide a method for determination of properties, in particular MSE, of cuttings from rock drilling in real-time using rock cuttings of the drilling process.

This and further objects are achieved by a method disclosed and claimed.

The method according to the invention provides property data from cuttings in that energy data is measured directly at rock cuttings as a rock property in an environment with less influence of other external factors and in real-time. In this way, reliable information about rock properties is available immediately at the rig site to make decisions regarding amongst others safety and optimization of the drilling process.

In the invention any motor can be used as a drive for the rolls provided the energy consumption can be determined properly.

In a preferred embodiment of the invention the motor is an electric motor and that the electric energy applied by the electric motor is measured, as in this way the energy can be measured very easily and precisely.

In this case the specific energy (MSE) can preferably be calculated as $$MSE = \frac{U * \eta}{V_r} * \left[ \int_{t_s}^{t_e} I(t) dt \right]$$

where:
U=voltage,
I=electric current,
$V_r$=volume of rock cuttings,
η=mechanical efficiency of the crusher,
$t_s$=test start time,
$t_e$=test end time.

If in another preferred embodiment of the invention a fixed volume of rock cuttings is crushed data can be obtained which can be compared to existing data easily which improves optimization of the drilling process.

Another important strength parameter of rocks is cohesion and unconfined compressive strength (UCS). Cohesion is the shear strength component, that is not related to the friction forces of the rock particles. Cohesion depends mainly on the cementing material between the grains of the rock. UCS is a parameter used in drilling engineering to determine the rock strength, which can be used to avoid amongst others instability problems, stuck pipe, tight hole, wellbore collapse, pack off and sand production. Further, UCS can be used to determine drillability of rock.

To date mechanical properties of rocks such as UCS and cohesion need to be determined in a laboratory. These tests are expensive since they need drilled rock samples, have to be carried out by trained personnel and special equipment is required. Further, it is difficult to obtain a core from the well that is being drilled due to the high costs involved.

The invention allows for determination of cohesion and UCS of cuttings of rock and cement samples from MSE data derived according to the invention.

By processing the rock cuttings according to the invention, it is possible to correlate MSE with UCS and cohesion, and these characteristics are immediately available using a low cost device.

Accordingly, in an embodiment of the method according to the invention a correlation between MSE and cohesion is developed.

In another embodiment of the method according to the invention a correlation between MSE and UCS is developed.

Based on this correlation cohesion or UCS can be directly be derived from MSE data which have been obtained according to the invention.

BRIEF DESCRIPTION OF THE DRAWINGS

Other features and advantages of the invention will become more readily apparent from the following detailed description of exemplary and therefore not limiting examples taken in conjunction with the accompanying drawings, in which.

DESCRIPTION OF THE PREFERRED EMBODIMENTS

Figure 1:
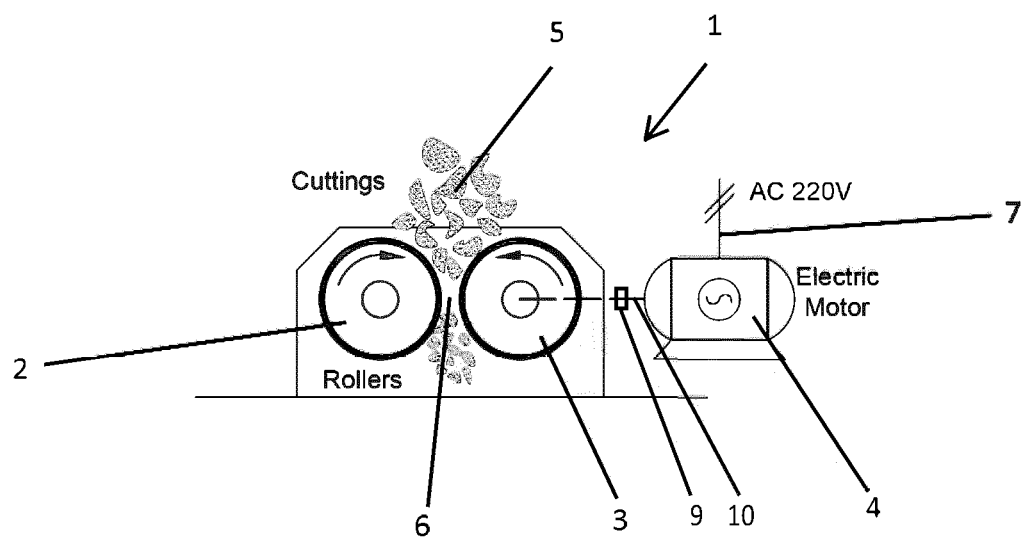
FIG. 1 is a device with which MSE data can be derived.

A device 1 for determination of properties, in particular mechanic specific energy (MSE) of cuttings from rock drilling, has two rollers 2, 3, at least one roller 3 being driven by a motor 4. Cuttings 5 from rock drilling are fed into a gap 6 and crushed into smaller pieces. The width of the gap 6 can be adjusted according to particular characteristics (e.g. size, rock type, rigidity) of the cuttings.

The applied energy for crushing the cuttings is measured and represents—related to the passed cutting mass or volume—the MSE. The MSE necessary to crush the cuttings can be calculated in that the power of the motor 4 is integrated over a time interval necessary to crush a particular amount of rock cuttings. In an alternative embodiment a particular time interval can be set and cuttings are supplied to the gap 6 as long as the time interval lasts. Of course in this latter case it is necessary to measure the mass or volume of crushed cuttings after the process.

In case the motor 4 is an electric motor the current in the power line 7 is measured and recorded during the test and the mechanic specific energy MSE necessary to crush the rock cuttings 5 is calculated as follows:

$$MSE = \frac{U * \eta}{V_r} * \left[ \int_{t_s}^{t_e} I(t) dt \right]$$

where:
U=voltage,
I=electric current,
$V_r$=volume of rock cuttings,
η=mechanical efficiency of the crusher,
$t_s$=test start time,
$t_e$=test end time.

Figure 2:
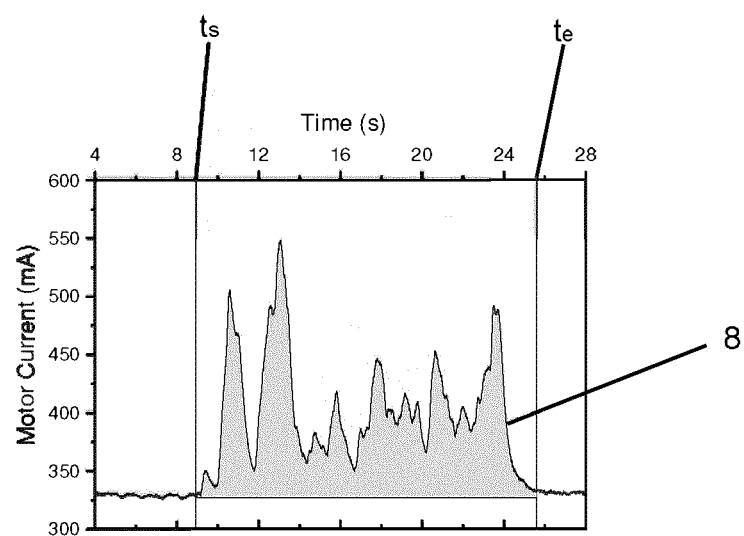
FIG. 2 is a plot showing the current versu time of a single test with the device of FIG. 1.

FIG. 2 is a plot of current versus time. The integral means the area below the curve 8 between test start time $t_s$ and test end time $t_e$ which is the measured current of the motor 4.

The MSE can be expressed in MPa, and it can be used as an indicator of the strength of the crushed rock.

The inventors found out that MSE measured and calculated as mentioned before shows a very good correlation to the unconfined compressive strength (UCS) and cohesion of rock cuttings. Therefore, based on this correlation UCS and cohesion can easily be derived from the MSE data.

In another embodiment of the application MSE is determined via the torque applied by the motor 4 to the driven roller 2. The torque can for example be determined by a torque meter 9 attached to the output shaft 10 of the motor 4.

In this case the mechanic specific energy MSE can be calculated as $$MSE = \frac{\pi * \eta}{30 * V_r} \left[ \int_{t_s}^{t_e} T(t) * n(t) * dt \right]$$

where:
MSE=mechanic specific energy,
T=torque,
n=rotational speed
Vr=volume of rock cuttings (6),
η=mechanical efficiency of the crusher,
$t_s$=test start time, and
$t_e$=test end time.

Instead of calculating MSE via an integral MSE can also be calculated as a sum of the product of individual records of the torque $T_i$ and the rotational speed $n_i$ and the time between two readings $$\left[ \int_{t_s}^{t_e} T(t) \cdot n(t) \cdot dt \right] \rightarrow \sum_{t_s}^{t_e} [T_i * n_i * \Delta t]$$

In this case the mechanic specific energy MSE can be calculated as $$MSE = \frac{\pi * \eta}{30 * V_r} \left[ \sum_{t_s}^{t_e} [T_i * n_i * \Delta t] \right]$$

where:
MSE=mechanic specific energy,
$T_i$=torque,
$n_i$=rotational speed
Vr=volume of rock cuttings (6),
η=mechanical efficiency of the crusher,
Δt=time between to measurements
$t_s$=test start time, and
$t_e$=test end time.

Figure 5:
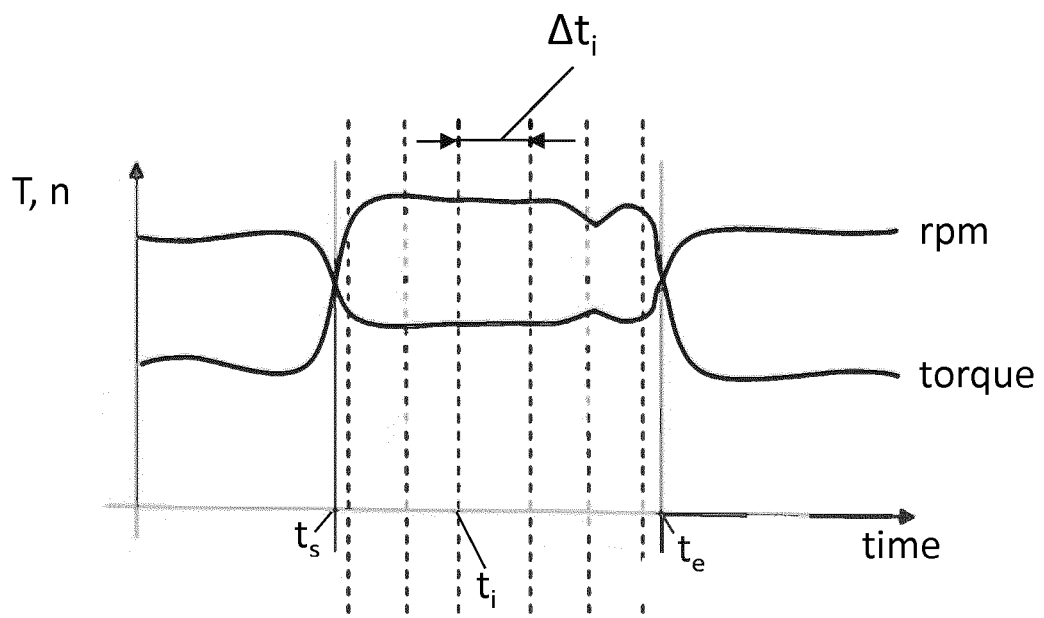
FIG. 5 is a plot showing the correlation of torque T and the number of revolutions n versus time.

This embodiment of the invention is shown in FIG. 5. FIG. 5 shows a plot of torque T and the number of revolutions n versus time. The torque $T_i$ is captured at several times $t_i$ and the product of torque $T_i$ and number of revolutions $n_i$ is calculated each time. The more measurements are made in the time interval between test start time $t_s$ and test end time $t_e$ and the shorter Δt is the more precise is the calculation of the energy provided by motor 4.

Figure 3:
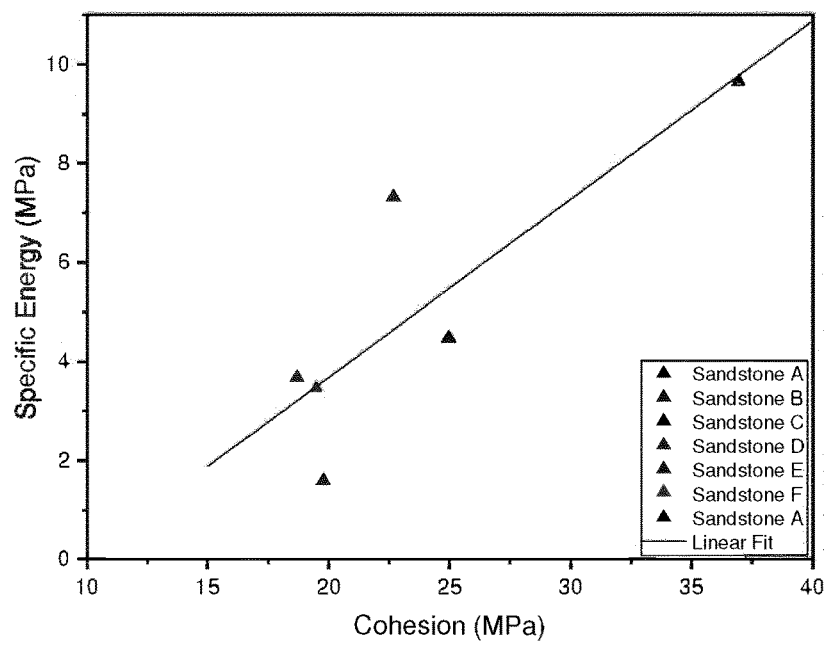
FIG. 3 is a plot showing the correlation between cohesion and MSE.

FIG. 3 is a plot showing the correlation between cohesion and MSE. In a first step a correlation between MSE and cohesion had to be developed using standard testing methods in a laboratory for determination of cohesion of a particular rock type which on the other hand has been tested with the device 1 of FIG. 1.

Figure 4:
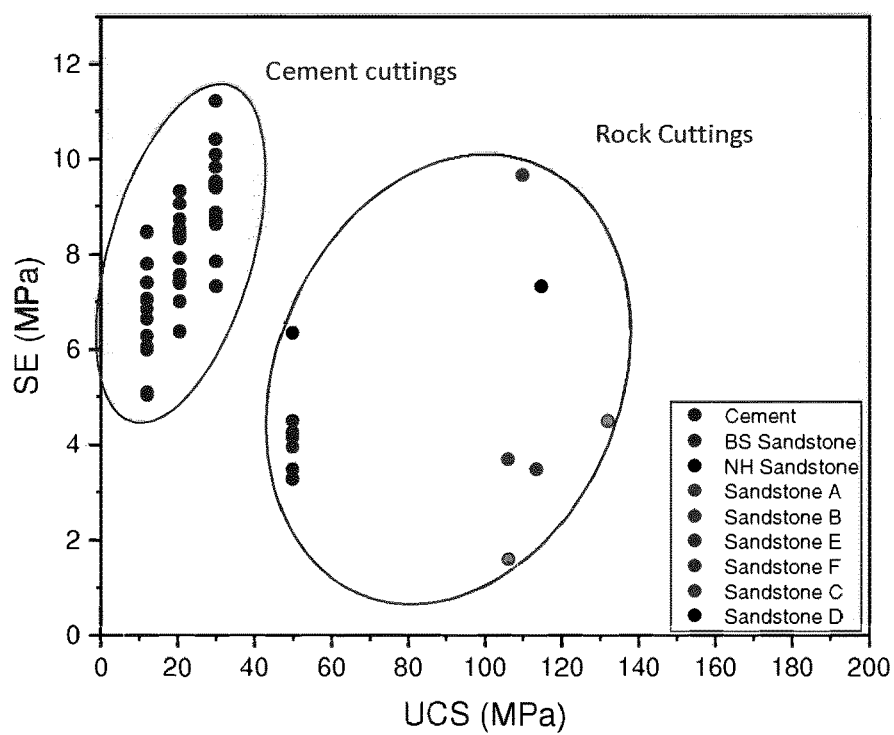
FIG. 4 is a plot showing the correlation between MSE and UCS.

FIG. 4 is a plot showing the correlation between UCS and MSE. As was the case with the relation between MSE and cohesion also in case of the correlation between UCS and MSE in a first step a correlation between MSE and UCS had to be developed using standard testing methods in a laboratory for determination of UCS of a particular rock type which on the other hand has been tested with the device 1 of FIG. 1.

Several tests were performed with the device 1 using different cement samples and rock samples. It is evident that the correlation of cohesion of cement samples is good as the cement does not have predominant grains; it is a homogeneous material with the same properties in the whole body. Unlike the cement, the sandstones tested are composed of grains of minerals and a cementing material between the grains that holds them together and may be composed of a matrix of silt or clay-size particles that fill the space between the grains. Although the UCS of both materials is the same (macro scale), there is a difference in the MSE required to crush a rock, since in a small scale (cuttings) the grain size and the cementing material acquire more importance in the crushing process.

After having determined the correlations between MSE, UCS and cohesion, respectively, these two correlations can be used to determine the properties of cement and rocks using cuttings from these materials after having tested these materials with the device 1 of FIG. 1 according to the method of the invention.

The invention claimed is:

1. A method for determining properties of cuttings from rock drilling in which the cuttings are crushed between at least two rollers, at least one of the at least two rollers being driven by a motor, the method comprising:
determining a mechanic specific energy of the cuttings by measuring electric energy applied by the motor, the mechanic specific energy being calculated as $$MSE = \frac{U * \eta}{V_r} * \left[ \int_{t_s}^{t_e} I(t) dt \right]$$

where:
MSE=the mechanic specific energy,
U=a voltage,
I=an electric current,
$V_r$=a volume of rock cuttings,
η=a mechanical efficiency of the at least two rollers,
$t_s$=a test start time, and
$t_e$=a test end time.

2. The method of claim 1, wherein the motor is an electric motor and the electric energy applied by the electric motor is measured.

3. The method as claimed in claim 2, wherein a fixed amount of rock cuttings is crushed.

4. The method as claimed in claim 2, wherein a fixed time is set to crush rock cuttings.

5. The method of claim 1, wherein a torque applied by the motor is measured.

6. The method as claimed in claim 5, wherein a fixed amount of rock cuttings is crushed.

7. The method as claimed in claim 5, wherein a fixed time is set to crush rock cuttings.

8. The method as claimed in claim 1, wherein a fixed amount of rock cuttings is crushed.

9. The method as claimed in claim 1, wherein a fixed time is set to crush rock cuttings.

10. The method as claimed in claim 1, wherein a correlation between the mechanic specific energy and unconfined compressive strength is developed, and
based on the correlation, unconfined compressive strength is derived from mechanic specific energy data.

11. The method as claimed in claim 1, wherein a correlation between the mechanic specific energy and cohesion is developed, and
based on the correlation, cohesion is derived from mechanic specific energy data.

12. A method for determining properties of cuttings from rock drilling in which the cuttings are crushed between at least two rollers, at least one of the at least two rollers being driven by a motor, the method comprising:
determining a mechanic specific energy of the cuttings by measuring electric energy applied by the motor,
wherein a torque applied by the motor is measured,
wherein the electric energy applied by the motor is calculated as $$MSE = \frac{\pi * \eta}{30 * V_r} \left[ \int_{t_s}^{t_e} T(t) * n(t) * dt \right]$$

where:
MSE=the mechanic specific energy,
T=the torque,
n=a rotational speed,
$V_r$=a volume of rock cuttings,
η=a mechanical efficiency of the at least two rollers,
$t_s$=a test start time, and
$t_e$=a test end time.

13. The method as claimed in claim 12, wherein a fixed amount of rock cuttings is crushed.

14. The method as claimed in claim 12, wherein a fixed time is set to crush rock cuttings.

15. A method for determining properties of cuttings from rock drilling in which the cuttings are crushed between at least two rollers, at least one of the at least two rollers being driven by a motor, the method comprising:
determining a mechanic specific energy of the cuttings by measuring electric energy applied by the motor,
wherein a torque applied by the motor is measured,
wherein the electric energy applied by the motor is calculated as $$MSE = \frac{\pi * \eta}{30 * V_r} \left[ \sum_{t_s}^{t_e} [T_i * n_i * \Delta t] \right]$$

where:
MSE=the mechanic specific energy,
$T_i$=the torque,
$n_i$=a rotational speed,
Vr=a volume of rock cuttings,
η=a mechanical efficiency of the at least two rollers,
Δt=a time between two measurements,
$t_s$=a test start time, and
$t_e$=a test end time.

16. The method as claimed in claim 15, wherein a fixed amount of rock cuttings is crushed.

17. The method as claimed in claim 15, wherein a fixed time is set to crush rock cuttings.

\* \* \* \* \*